United States Patent
Xu et al.

(10) Patent No.: US 11,630,113 B2
(45) Date of Patent: Apr. 18, 2023

(54) METHOD FOR ASSIGNING ANTIBODY STANDARD AND DETERMINING MINIMUM DETECTION LIMIT OF ANTIBODY DETECTION REAGENT

(71) Applicant: LANSION BIOTECHNOLOGY CO., LTD., Jiangsu (CN)

(72) Inventors: Xingshang Xu, Jiangsu (CN); Jeffery Chen, Jiangsu (CN); Peng Wang, Jiangsu (CN)

(73) Assignee: LANSION BIOTECHNOLOGY CO., LTD., Jiangsu (CN)

( * ) Notice: Subject to any disclaimer, the term of this patent is extended or adjusted under 35 U.S.C. 154(b) by 0 days.

(21) Appl. No.: 17/762,088

(22) PCT Filed: Jul. 16, 2021

(86) PCT No.: PCT/CN2021/106796
§ 371 (c)(1),
(2) Date: Mar. 21, 2022

(87) PCT Pub. No.: WO2022/012673
PCT Pub. Date: Jan. 20, 2022

(65) Prior Publication Data
US 2022/0326253 A1    Oct. 13, 2022

(30) Foreign Application Priority Data
Jul. 15, 2020  (CN) .......................... 202010679432.5

(51) Int. Cl.
*G01N 33/53* (2006.01)
*G01N 33/68* (2006.01)
*G01N 33/543* (2006.01)

(52) U.S. Cl.
CPC ....... *G01N 33/6854* (2013.01); *G01N 33/543* (2013.01)

(58) Field of Classification Search
CPC .... G01N 33/53; G01N 333/543; G01N 33/68; G01N 33/6854; Y10S 436/826; Y10S 435/967
See application file for complete search history.

(56) References Cited

U.S. PATENT DOCUMENTS

| | | | | |
|---|---|---|---|---|
| 2005/0176157 | A1* | 8/2005 | Vasilyeva | G01N 27/44791 436/516 |
| 2013/0337438 | A1* | 12/2013 | Mori | G01N 33/57411 435/5 |
| 2017/0028046 | A1* | 2/2017 | Sawada | A61P 7/10 |
| 2017/0112914 | A1* | 4/2017 | Ballou, Jr. | A61P 33/06 |
| 2020/0318136 | A1* | 10/2020 | Wang | C07K 16/1018 |

FOREIGN PATENT DOCUMENTS

| | | |
|---|---|---|
| CN | 103033621 | 4/2013 |
| CN | 103792200 | 5/2014 |
| CN | 106706924 | 5/2017 |
| CN | 107267624 | 10/2017 |
| CN | 110646614 | 1/2020 |
| CN | 112198318 | 1/2021 |
| EP | 0353895 | 2/1990 |

OTHER PUBLICATIONS

Ho et al., Circulating antibodies against Plasmodium falciparum histidine-rich proteins 2 interfere with antigen detection by rapid diagnostic test, Malaria Journal 2014, 13, pp. 1-12. (Year: 2014).*
"International Search Report (Form PCT/ISA/210) of PCT/CN2021/106796," dated Sep. 28, 2021, with English translation thereof, pp. 1-4.
"Written Opinion of the International Searching Authority (Form PCT/ISA/237) of PCT/CN2021/106796," dated Sep. 28, 2021, pp. 1-5, English portions only.

* cited by examiner

*Primary Examiner* — Gary Counts
(74) *Attorney, Agent, or Firm* — JCIPRNET

(57) ABSTRACT

A method for assigning an antibody standard and determining a minimum detection limit of an antibody detection reagent specifically includes the following steps: S1, determination of a neutralized antigen equivalent of an antibody standard or a sample: an antigen with a known purity and concentration is subjected to a gradient dilution using a matrix, an equal amount of an antibody standard or antibody-containing sample is added to each of the gradient diluents with different concentrations respectively, and after a reaction, each mixture is subjected to an antibody detection using a first antibody detection reagent, to determine the neutralized antigen equivalent of the antibody standard or sample; S2, determination of an antibody titer of the sample; and S3, acquisition of the minimum detection limit of an antibody detection reagent.

10 Claims, No Drawings

METHOD FOR ASSIGNING ANTIBODY STANDARD AND DETERMINING MINIMUM DETECTION LIMIT OF ANTIBODY DETECTION REAGENT

CROSS-REFERENCE TO RELATED APPLICATION

This is a 371 application of the International PCT application serial no. PCT/CN2021/106796, filed on Jul. 16, 2021, which claims the priority benefits of China Application No. 202010679432.5, filed on Jul. 15, 2020. The entirety of each of the above-mentioned patent applications is hereby incorporated by reference herein and made a part of this specification.

TECHNICAL FIELD

The present invention relates to the technical field of medical testing, and in particular to a method for assigning an antibody standard and determining the minimum detection limit of an antibody detection reagent.

DESCRIPTION OF RELATED ART

IVD (In Vitro Diagnosis) medical devices refer to products used for testing samples (blood, body fluid, tissues and the like) of human body, to acquire clinical diagnostic information, including reagents, calibrators, control substances, apparatuses or systems. A diagnostic reagent is one of the basic tools to detect whether a patient is sick and how sick, and whether the results are accurate or not directly affects a doctor's diagnosis as well as the physical health and life safety of the patient. With the advancement of modern medical technology, higher precision requirements are imposed on the results of medical tests, thereby imposing an increasingly higher requirement on the quality of IVD products.

Preparation of standard substances (e.g., international standards, national standards and enterprise standards and calibrators for clinical applications) and metrological traceability thereof are preconditions for acquiring precise measurement results. Due to poor storage stability of antibodies, the activity of the antibodies gradually declines as the preservation time increases even at cryopreservation; and the activity of the antibodies is mostly represented by a relative dilution titer, making objective and precise quantification very difficult. Therefore, the preparation of standards or reference substances for various antibodies is very difficult. At present, there is a lack of commercial supply of relevant antibody standards both at home and abroad, thereby bringing many insurmountable difficulties to the production and application of antibody detection reagents.

On the other hand, an important performance parameter of an antibody detection reagent is detection limit. The detection limit is a minimum value at which a biological sample is treated and tested according to the requirements of an analytical method and can be distinguished from the noise to report the presence of the measured object with a specific confidence level. It is also used to refer to the minimum detectable concentration. Therefore, the detection limit is also a quantitative indicator. Due to the lack of antibody standards, the minimum detection limit of an antibody detection reagent cannot be precisely determined.

Therefore, it is necessary to develop a method capable of accurately quantifying antibodies. Although the antibodies have unstable activity, antigens corresponding to the antibodies are often stable and can be accurately quantified. Since the antigens can undergo a neutralizing reaction with the antibodies (the neutralizing reaction is a reaction between an antigenic determinant and an antibody recognition end Fab), the antibody activity can be quantified according to the quantity of antigens required for neutralizing the activity of the antibodies, that is, the antibodies are assigned. The quantity of corresponding antigens required for neutralizing antibodies in a matrix (serum) per unit volume is called NAE (Neutralized Antigen Equivalent) of the antibodies. The size of NAE is used to quantify the antibodies, and a larger NAE of antibodies indicates more antibodies in a matrix per unit volume. Accordingly, the antibodies can be quantified, to assign an antibody standard substance and determine the minimum detection limit of an antibody detection reagent.

SUMMARY

A technical problem to be solved by the present invention is to provide a method for assigning an antibody standard and determining the minimum detection limit of an antibody detection reagent. The method can solve a problem that the minimum detection limit of currently available antibody detection reagents cannot be certified or accurately certified, and can also be used as a method for assigning the activity of an antibody standard.

In order to solve the technical problem, a technical solution adopted by the present invention is: the method for assigning an antibody standard and determining the minimum detection limit of an antibody detection reagent, specifically comprising the following step:

S1, determination of a neutralized antigen equivalent of an antibody standard or a sample: an antigen with a known purity and concentration is subjected to a gradient dilution using a matrix, to obtain a plurality of gradient diluents with different concentrations; an equal amount of an antibody standard or an antibody-containing sample is added to each of the gradient diluents with different concentrations respectively, and after a reaction, each mixture is subjected to an antibody detection using a first antibody detection reagent, to determine the neutralized antigen equivalent of the antibody standard or sample; where in the step S1, the method for the determination of the neutralized antigen equivalent of the antibody standard or sample is a method for assigning an antibody quantity in a certain volume. The unit of measurement for the neutralized antigen equivalent of antibodies in the antibody standard or sample in a certain volume is represented by a mass-volume concentration of antigens that can be neutralized by the antibodies; and in order to particularly clarify that a mass number in the mass-volume unit is the quantity of corresponding neutralizing antigens, the mass unit is followed by "NAE", for example, 1 ng NAE/mL, 1 µg NAE/mL, 1 mg NAE/mL, etc.

The matrix refers to all components in a specimen, except an analyte. As for the measurement of serum cholesterol (Chol), the matrix refers to all components in the serum, except the Chol. Since antigens or antibodies often exist in serum, the matrix of the present invention specifically refers to the serum components (or buffer components for dilution) in the "antigen with a known purity and concentration", except the "antigen"; and the serum components (or buffer components for dilution) in the "antibody standard or antibody-containing sample", except the "antibody standard" and the "antibody".

The present invention is further improved by further comprising the following steps: S2, determination of an antibody titer of the sample: the antibody-containing sample in the step S1 is subjected to a gradient dilution using a matrix, to obtain gradient diluents with different dilutions; and a gradient diluent of each dilution is subjected to an antibody detection using a second antibody detection reagent, to determine the antibody titer of the sample; and S3, acquisition of the minimum detection limit of an antibody detection reagent: the neutralized antigen equivalent of the sample determined in the step S1 is multiplied by the antibody titer of the sample determined in the step S2, to acquire the minimum detection limit of the second antibody detection reagent.

In the technical solution, the method for assigning an antibody standard and determining the minimum detection limit of an antibody detection reagent first determines the neutralized antigen equivalent (A) of the antibody standard or sample, and then determines the antibody titer (B) of the sample, and accordingly, the minimum detection limit of the antibody detection reagent=A*B. Because the antigens are often stable and quantifiable and can undergo a neutralizing reaction with the antibodies and the neutralizing reaction is a reaction between an antigenic determinant and an antibody recognition end Fab, the minimum detection limit of the antibodies is determined using a specific antibody detection reagent, where the antigen adopted in the step S1 is of a known purity and concentration, and after a gradient dilution, an equal amount of an antibody standard or antibody-containing sample is added; the sample can be a mixed sample or an original sample and can be diluted appropriately and accurately, and is tested after a reaction. Among all gradient dilutions, one will present a positive reaction, and an antigen quantity of a dilution with a higher concentration immediately before that presenting the positive reaction is the neutralized antigen equivalent of the antibody standard or sample; and if the sample is a diluted sample, a dilution factor needs to be taken into account. The antibody titer of the sample in the step S2 is tested after a gradient dilution using the same antibody-containing sample as in the step S1; and among all gradient dilutions, one will present a negative reaction, and the dilution of a diluent with a higher concentration immediately before that presenting the negative reaction is the antibody titer of the sample. The first antibody detection reagent in the step S1 and the second antibody detection reagent in the step S2 can be different detection reagents; and the first antibody detection reagent used in the step S1 can be a detection reagent which is superior to and has a higher precision and a lower detection limit than the second antibody detection reagent used in the step S2.

The present invention is further improved by further comprising a step S4, confirmation of the minimum detection limit of the antibody detection reagent: at least three antibody-containing samples are treated according to the steps S1-S3, to acquire the minimum detection limit of the second antibody detection reagent; if the acquired minimum detection limit of the antibody-containing samples is consistent with the minimum detection limit acquired in the step S3, the antibody-containing samples are respectively diluted to a concentration of the minimum detection limit, and tested repeatedly; and if the positive rates are ≥90%, the minimum detection limit of the second antibody detection reagent passes the confirmation. At least 3 representative clinical samples containing to-be-detected antibodies from different sources are selected respectively for confirmation. First, the neutralized antigen equivalent (A) is determined; the antibody titer (B) is determined; the minimum detection limit of the antibody detection reagent=A*B; and then, the antibody-containing samples are respectively diluted to a concentration of the minimum detection limit, to confirm whether the minimum detection limit acquired through the steps S1-S3 is accurate.

The present invention is further improved by further comprising a step S5, verification of the minimum detection limit of an antibody detection reagent: at least three antibody-containing samples are respectively diluted to a concentration of the minimum detection limit, and tested repeatedly; and if the positive rates reach 90-95%, the minimum detection limit passes the verification. At least 3 clinical samples (different from the samples used for the confirmation of the minimum detection limit in the step S4) with temporal and regional characteristics are selected, and repeatedly tested by preferably 20 times; and through the verification, it can be further confirmed whether the minimum detection limit of the antibody detection reagent acquired through the steps S1-S3 is accurate.

As a preferred technical solution of the present invention, the dilutions of the gradient dilution of the antigen in the step S1 are: 1:2, 1:4, 1:8, 1:16, 1:32, 1:64, 1:128 and 1:256 respectively.

As a preferred technical solution of the present invention, in the step S1, an equal amount of an antibody standard or a specific antibody-containing sample is added to each gradient diluent respectively; after a reaction of 30 min at 37° C., each mixture is tested using a first antibody detection reagent respectively; and if a mixture of a certain dilution presents a positive reaction in the test result, an antigen quantity of a mixture with a higher concentration immediately before the present mixture is determined as the neutralized antigen equivalent of the antibody standard or sample.

As a preferred technical solution of the present invention, the gradient dilutions of the antibody-containing sample in the step S2 are 1:2, 1:4, 1:8, 1:16, 1:32, 1:64 and 1:128 respectively; in the step S2, the diluent of each dilution is subjected to an antibody detection using the second antibody detection reagent; and if a diluent of a certain dilution presents a negative reaction in the detection result, the dilution of a diluent with a higher concentration immediately before the present diluent is determined as the antibody titer of the sample.

As a preferred technical solution of the present invention, in the step S3, the neutralized antigen equivalent of the sample determined in the step S1 is multiplied by the antibody titer of the sample determined in the step S2, to acquire the minimum detection limit of the second antibody detection reagent.

As a preferred technical solution of the present invention, in the step S4, if the positive rates are lower than 90% after the repeated tests, the antibody titer in the step S2 is adjusted by selecting a dilution immediately before the currently determined antibody titer as a new antibody titer, and then repeated tests are performed until the positive rates are ≥90% and at this time, the confirmed minimum detection limit is recalculated according to the new antibody titer.

As a preferred technical solution of the present invention, the method further includes a step S5, verification of the minimum detection limit of an antibody detection reagent: at least three antibody-containing samples are respectively diluted to a concentration of the minimum detection limit, and tested 3 times first; if the 3 tests are all positive, the verification is passed; if one of the 3 tests is negative, another 7 tests are performed, and if all of the 7 tests are positive, the verification is passed; if two of the 3 tests are negative, another 18 tests are performed, and if all of the 18 tests are positive, the verification is passed; and if the 3 tests are all negative, the verification fails. When 20 or more tests are performed at a time, more time will be consumed, and then the progressive way can be adopted for the verification of the minimum detection limit of the second antibody detection reagent.

As a preferred technical solution of the present invention, in the step S4, at least three representative clinical samples containing to-be-detected antibodies from different sources are respectively selected for the confirmation of the minimum detection limit of the second antibody detection reagent; and in the step S5, at least 3 clinical samples with temporal and regional characteristics and different from the samples used for the confirmation of the minimum detection limit in the step S4 are selected for the verification of the minimum detection limit of the second antibody detection reagent.

As a preferred technical solution of the present invention, the first antibody detection reagent in the step S1 is an antibody detection reagent which is superior to or the same as the second antibody detection reagent used in the step S2; and the antibody detection reagent used in the step S1 can have a higher precision and a lower detection limit than the antibody detection reagent used in the step S2.

Compared with the prior art, the method for assigning an antibody standard and determining the minimum detection limit of an antibody detection reagent has the following beneficial effects: since antigens have stable properties and can be precisely quantified while antibodies have unstable properties, the method employs antigens to assign the antibody standard, and can be used for preparing enterprise standards and even national standards; the method can precisely determine the minimum detection limit of an antibody detection agent, thereby solving a problem that the minimum detection limit of currently available antibody detection reagents cannot be certified or accurately certified, and representing an innovative solution for precisely determining the minimum detection limit of an antibody detection reagent at present; and through precise determination of the minimum detection limit of an antibody detection agent, stable quality of the reagent can be guaranteed and the detection accuracy and clinical efficiency are improved.

DESCRIPTION OF THE EMBODIMENTS

In order to deepen understanding of the present invention, the present invention will be further elaborated on with reference to accompanying drawings and embodiments; and the embodiments are only intended to explain the present invention, and do not constitute a limitation on the protection scope of the present invention.

Embodiment 1. A method for assigning an antibody standard, specifically including the following step:

S1, determination of a neutralized antigen equivalent of an antibody standard: an antigen with a known purity and concentration is subjected to a gradient dilution using a matrix, to obtain a series of gradient diluents with different concentrations; an equal amount of an antibody standard is added to each of the diluents with different concentrations respectively, and after a reaction, each mixture is subjected to an antibody detection using a first antibody detection reagent, to determine the neutralized antigen equivalent of the antibody standard, thereby assigning the antibody standard, where a quantity value of antibodies in the antibody standard is represented by a mass-volume concentration unit of the neutralized antigen equivalent thereof.

The embodiment is used for preparing an antibody standard (standard substance) for novel coronavirus (COVID-19), and an assigning method thereof is as follows:

collecting high-titer antibody serum of a convalescent COVID-19 patient and mixing well, as an antibody standard; and determining a neutralized antigen equivalent of the antibody standard: a recombinant novel COVID-19 antigen (S protein) with a concentration of 400 µg/mL was subjected to a gradient dilution using a matrix (negative serum), with dilutions of 1:2, 1:4, 1:8, 1:16, 1:32, 1:64, 1:128 and 1:256 respectively, to obtain diluents of 50 µL each; an equal volume of 50 µL of the antibody serum was added to each gradient diluent respectively; after a reaction of 30 min at 37° C., the mixture was subjected to an antibody detection using an antibody detection reagent; the mixture with a dilution of 1:64 presented a positive reaction, and then the antigen quantity in the mixture with a dilution of 1:32 was determined as the neutralized antigen equivalent of the 50 µL antibody standard, and an antibody concentration of the antibody standard was calculated as 400 µg/mL÷32=12.5 µg NAE/mL, that is, the antibody standard for novel coronavirus (COVID-19) was assigned 12.5 µg NAE/mL; and the antibody serum was sub-packaged and cryopreserved.

In use, the sub-packaged and cryopreserved antibody serum is taken out and recovered to room temperature; the neutralized antigen equivalent of the antibody standard is redetermined using the above-mentioned method, namely, reassigning the antibody standard, to guarantee precise determination of the quantity value of the antibody standard and avoid clinical diagnostic errors caused by a decrease in the activity of the antibody standard.

With the above-mentioned method for assigning an antibody standard, namely, a method for determining a neutralized antigen equivalent of a sample, the minimum detection limit of the antigen detection reagent can be acquired through the steps S2 and S3, and confirmed and verified through the steps S4 and S5 (refer to the content of Embodiment 2 below for details).

Embodiment 2: A method for determining the minimum detection limit of an antibody detection reagent, specifically including the following steps:

S1, determination of a neutralized antigen equivalent of a sample: an antigen with a known purity and concentration is subjected to a gradient dilution using a matrix, with dilutions of 1:2, 1:4, 1:8, 1:16, 1:32, 1:64, 1:128 and 1:256 respectively, to obtain a plurality of gradient diluents with different concentrations; an equal amount of a specific antibody-containing sample is added to the diluent of each dilution respectively; after a reaction of 30 min at 37° C., each mixture is tested using a specific antibody detection reagent (first antibody detection reagent) respectively; and if a mixture of a certain dilution presents a positive reaction in the test result, an antigen quantity of a mixture with a higher concentration immediately before the present mixture is determined as the neutralized antigen equivalent of the sample;

S2, determination of an antibody titer of the sample: the antibody-containing sample is subjected to a gradient dilution using a matrix, with dilutions of 1:2, 1:4, 1:8, 1:16, 1:32, 1:64 and 1:128 respectively, to obtain gradient diluents with different dilutions; the diluent of each dilution is subjected to an antibody detection using a second antibody detection reagent; if a diluent of a certain dilution presents a negative reaction in the detection result, the dilution of a diluent with a higher concentration immediately before the present diluent is determined as the antibody titer, thereby determining the antibody titer; and S3, acquisition of the minimum detection limit of an antibody detection reagent: the neutralized antigen equivalent of antibodies in the sample acquired in the step S1 is multiplied by the antibody titer of the sample determined in the step S2, to acquire the minimum detection limit of the second antibody detection reagent.

The minimum detection limit of the antibody detection reagent can be confirmed and verified as follows:

S4, confirmation of the minimum detection limit of the antibody detection reagent: at least 3 representative clinical samples containing to-be-detected antibodies from different sources are selected respectively; the 3 clinical samples containing to-be-detected antibodies are treated according to the steps S1-S3 to acquire the minimum detection limit of the antibody detection reagent; if the acquired minimum detection limit of the antibody-containing samples is consistent with the minimum detection limit determined in the step S3, the antibody-containing samples are respectively diluted to a concentration of the minimum detection limit, and tested repeatedly for 20 times; and if the positive rates are ≥90%, the minimum detection limit of the second antibody detection reagent passes the confirmation;

if the positive rates are lower than 90% after the repeated tests, the antibody titer in the step S2 is adjusted by selecting a dilution immediately before the currently determined antibody titer as a new antibody titer, and then repeated tests are performed until the positive rates are ≥90% and at this time, the confirmed minimum detection limit is recalculated according to the new antibody titer;

S5, verification of the minimum detection limit of the antibody detection reagent: 3 clinical samples (different from the samples used for the confirmation of the minimum detection limit in the step S4) with temporal and regional characteristics are selected; the 3 clinical samples are respectively diluted to a concentration of the minimum detection limit, and tested 20 times; and if the positive rates reach 90-95%, the minimum detection limit passes the verification;

or a method for the verification of the minimum detection limit of the antibody detection reagent in the step S5 is: 3 clinical samples are respectively diluted to a concentration of the minimum detection limit, and tested 3 times first; if the 3 tests are all positive, the verification is passed; if one of the 3 tests is negative, another 7 tests are performed, and if all of the 7 tests are positive, the verification is passed; if two of the 3 tests are negative, another 18 tests are performed, and if all of the 18 tests are positive, the verification is passed; and if the 3 tests are all negative, the verification fails (when 20 or more tests are performed at a time, more time will be consumed, and then the progressive way can be adopted for the verification of the minimum detection limit of the second antibody detection reagent).

When the method for determining the minimum detection limit of an antibody detection reagent is applied to a specific detection to determine the minimum detection limit of an RSV (respiratory syncytial virus) IgM antibody detection kit (colloidal gold method), the method specifically includes the following steps:

test materials:
antigen: RSV F protein, 1,000 μg/mL, purchased from Absolute Antibody;
detection kit: RSV IgM antibody detection kit (colloidal gold method), purchased from Beijing Innovita Bio-Tech Co., Ltd.;
negative serum: purchased from Beijing JKHD Bio-Tech Co., Ltd.;

S1, determination of a neutralized antigen equivalent of a sample:

S1-1, antigen dilution: the antigen was subjected to a gradient dilution using a matrix—the negative serum, where the dilutions of the RSV F protein were 1:2, 1:4, 1:8, 1:16, 1:32, 1:64, 1:128 and 1:256 respectively, and each dilution resulted in a 50 μL sample, to obtain a plurality of gradient diluents with different concentrations;

S1-2, test after antigen/antibody incubation: a 50 μL sample containing RSV IgM was added to each gradient diluent respectively; after a water-bath treatment of 30 min at 37° C., each mixture was tested using the RSV IgM antibody detection kit (colloidal gold method); data were recorded in Table 1;

TABLE 1

Result Data of Test after Antigen/Antibody Incubation

| | Antigen Dilution Gradient | | | | | | | |
|---|---|---|---|---|---|---|---|---|
| | 1:2 | 1:4 | 1:8 | 1:16 | 1:32 | 1:64 | 1:128 | 1:256 |
| Negative/Positive | − | − | − | − | − | − | + | + |

S1-3, determination of a neutralized antigen equivalent of the sample: if a mixture of a certain dilution presented a positive reaction in the test result, an antigen quantity of a mixture with a higher concentration immediately before the present mixture was determined as the neutralized antigen equivalent of antibodies in the sample, that is, the neutralized antigen equivalent of the sample containing RSV IgM was 1,000 fig/mL÷64=15.625 μg NAE/mL;

S2, determination of an antibody titer of the sample:

S2-1, sample dilution: the sample containing RSV IgM was subjected to a gradient dilution using the negative serum, where the dilutions of the sample were 1:2, 1:4, 1:8, 1:16, 1:32, 1:64 and 1:128 respectively, to obtain gradient diluents with different concentrations;

S2-2, antibody detection: the diluent of each dilution was subjected to an antibody detection using the RSV IgM antibody detection kit (colloidal gold method); data were recorded in Table 2;

TABLE 2

Result Data of Sample (Antibody) Detection

| | Sample (Antibody) Dilution Gradient | | | | | | |
|---|---|---|---|---|---|---|---|
| | 1:2 | 1:4 | 1:8 | 1:16 | 1:32 | 1:64 | 1:128 |
| Negative/Positive | + | + | + | + | + | − | − |

S2-3, determination of an antibody titer of the sample: if a diluent of a certain dilution presented a negative reaction in the detection result, a dilution of a diluent with a higher concentration immediately before the present diluent was determined as the antibody titer, thereby determining the antibody titer of the sample, that is, the antibody titer was 1:32;

S3, acquisition of the minimum detection limit of the antibody detection reagent: the neutralized antigen equivalent of the sample determined in the step S1 was multiplied by the antibody titer of the sample determined in the step S2, to acquire the minimum detection limit of the second antibody detection reagent, that is, the minimum detection limit of the RSV IgM antibody detection kit (colloidal gold method) was 15.625 μg NAE/mL×(1:32)=0.488 μg NAE/mL.

The data of the above-mentioned embodiment was subjected to confirmation and verification in a step S4 and a step S5;

S4, confirmation of the minimum detection limit of the antibody detection reagent: at least 3 representative clinical samples containing to-be-detected antibodies from different sources were selected respectively; the 3 clinical samples containing to-be-detected antibodies were treated according to the steps S1-S3 to acquire the minimum detection limit of the antibodies; if the acquired minimum detection limit of the antibody-containing samples was consistent with the minimum detection limit determined in the step S3, the antibody-containing samples were respectively diluted to a concentration of the minimum detection limit, and tested repeatedly for 20 times; and if the positive rates were ≥90%, the minimum detection limit of the second antibody detection reagent passed the confirmation;

if the positive rates were lower than 90% after the repeated tests, the antibody titer in the step S2 was adjusted by selecting a dilution with a higher concentration immediately before the currently determined antibody titer as a new antibody titer, and then repeated tests were performed until the positive rates were ≥90% and at this time, the confirmed minimum detection limit was recalculated according to the new antibody titer;

S5, verification of the minimum detection limit of the antibody detection reagent: 3 clinical samples (different from the samples used for the confirmation of the minimum detection limit in the step S4) with temporal and regional characteristics were selected; the 3 clinical samples were respectively diluted to a concentration of the minimum detection limit, and tested repeatedly; and if the positive rates reached 90-95%, the minimum detection limit passed the verification;

or a method for the verification of the minimum detection limit of the antibody detection reagent in the step S5 were: 3 clinical samples were respectively diluted to a concentration of the minimum detection limit, and tested 3 times first; if the 3 tests were all positive, the verification was passed; if one of the 3 tests was negative, another 7 tests were performed, and if all of the 7 tests were positive, the verification was passed; if two of the 3 tests were negative, another 18 tests were performed, and if all of the 18 tests were positive, the verification was passed; and if the 3 tests were all negative, the verification failed (when 20 or more tests are performed at a time, more time will be consumed, and then the progressive way can be adopted for the verification of the minimum detection limit of the second antibody detection reagent).

For those of ordinary skill in the art, specific embodiments are only used for exemplary description of the present invention, and apparently, specific implementation of the present invention is not limited to the above-mentioned embodiments. Various unsubstantial improvements to the method conception and technical solution of the present invention, or direct applications of the conception and technical solution of the present invention to other occasions without improvement, are all within the protection scope of the present invention.

What is claimed is:

1. A method for assigning an antibody standard and detecting a minimum detection limit of an antibody detection reagent, specifically comprising the following steps:

S1, detection of a neutralized antigen equivalent of an antibody standard or an antibody-containing sample wherein an antigen with a known purity and concentration is subjected to a gradient dilution using a matrix, to obtain a series of antigen diluents with different dilutions; and an equal amount of the antibody standard or an equal amount of the antibody-containing sample is added to each of the antigen diluents respectively, and the antibody standard or the antibody-containing sample is bound to the antigen in the antigen diluents; after a reaction, each mixture is subjected to an antibody detection using a first antibody detection reagent; the antigen-unbound antibody standard or the antigen-unbound antibody-containing sample in each mixture is bound to and detected by the first antibody detection reagent and if a mixture of a certain antigen dilution presents a positive reaction in the test result, an antigen quantity of a mixture with a higher concentration immediately before the present mixture is detected as the neutralized antigen equivalent of the antibody standard or the antibody-containing sample;

S2, detection of an antibody titer of the antibody-containing sample wherein the antibody-containing sample in the step S1 is subjected to a gradient dilution using a matrix, to obtain a series of sample diluents with different dilutions; and the sample diluent of each dilution is subjected to an antibody detection using a second antibody detection reagent the antibody in the sample diluent of each dilution is bound to and detected by the second antibody detection reagent, to obtain the antibody titer of the antibody-containing sample; and S3, acquisition of the minimum detection limit of the second antibody detection reagent wherein the neutralized antigen equivalent of the antibody-containing sample acquired in the step S1 is multiplied by the antibody titer of the antibody-containing sample acquired in the step S2, to acquire the minimum detection limit of the second antibody detection reagent, wherein the first antibody detection reagent comprises a first binding agent specific for the antibody in the antibody standard or the antibody-containing sample, and the second antibody detection reagent comprises a second binding agent specific for the antibody in the antibody-containing sample.

2. The method for assigning the antibody standard and detecting the minimum detection limit of the antibody detection reagent according to claim 1, further comprising a step S4, confirmation of the minimum detection limit of the second antibody detection reagent wherein at least three antibody-containing samples are treated according to the steps S1-S3, to acquire the minimum detection limit of the second antibody detection reagent; if the acquired minimum detection limit of the antibody-containing samples is consistent with the minimum detection limit acquired in the step S3, the antibody-containing samples are respectively diluted to a concentration of the minimum detection limit, and tested repeatedly; and if the positive rates are ≥90%, the minimum detection limit of the second antibody detection reagent passes the confirmation.

3. The method for assigning the antibody standard and detecting the minimum detection limit of the antibody detection reagent according to claim 2, further comprising a step S5, verification of the minimum detection limit of the second antibody detection reagent wherein at least three antibody-containing samples are respectively diluted to a concentration of the minimum detection limit, and tested repeatedly; and if the positive rates reach 90-95%, the minimum detection limit of the second antibody detection reagent passes the verification.

4. The method for assigning the antibody standard and detecting the minimum detection limit of the antibody detection reagent according to claim 1, wherein the dilutions of the antigen diluents in the step S1 are: 1:2, 1:4, 1:8, 1:16, 1:32, 1:64, 1:128 and 1:256 respectively.

5. The method for assigning the antibody standard and detecting the minimum detection limit of the antibody detection reagent according to claim 4, wherein the reaction is performed for 30 min at 37° C.

6. The method for assigning the antibody standard and detecting the minimum detection limit of the antibody detection reagent according to claim 4, wherein the dilutions for diluting the antibody-containing sample in the step S2 are 1:2, 1:4, 1:8, 1:16, 1:32, 1:64 and 1:128 respectively; in the step S2, if a sample diluent of a certain dilution presents a negative reaction in the detection result, the dilution of a sample diluent with a higher concentration immediately before the present sample diluent is detected as the antibody titer.

7. The method for assigning the antibody standard and detecting the minimum detection limit of the antibody detection reagent according to claim 2, wherein in the step S4, if the positive rates are lower than 90% after the repeated tests, the antibody titer in the step S2 is adjusted by selecting a dilution immediately before the currently acquired antibody titer as a new antibody titer, and then repeated tests are performed until the positive rates are ≥90% and at this time, the confirmed minimum detection limit is recalculated according to the new antibody titer.

8. The method for assigning the antibody standard and detecting the minimum detection limit of the antibody detection reagent according to claim 4, further comprising a step S5, verification of the minimum detection limit of the second antibody detection reagent: at least three antibody-containing samples are respectively diluted to a concentration of the minimum detection limit, and tested 3 times first; if the 3 tests are all positive, the verification is passed; if one of the 3 tests is negative, another 7 tests are performed, and if all of the 7 tests are positive, the verification is passed; if two of the 3 tests are negative, another 18 tests are performed, and if all of the 18 tests are positive, the verification is passed; and if the 3 tests are all negative, the verification fails.

9. The method for assigning the antibody standard and detecting the minimum detection limit of the antibody detection reagent according to claim 3, wherein in the step S4, at least three representative clinical samples containing to-be-detected antibodies from different sources are respectively selected for the confirmation of the minimum detection limit of the second antibody detection reagent; and in the step S5, at least 3 clinical samples with temporal and regional characteristics and different from the samples used for the confirmation of the minimum detection limit of the second antibody detection reagent in the step S4 are selected for the verification of the minimum detection limit of the second antibody detection reagent.

10. The method for assigning the antibody standard and detecting the minimum detection limit of the antibody detection reagent according to claim 1, wherein the first antibody detection reagent in the step S1 is the antibody detection reagent the same as the second antibody detection reagent in the step S2.

* * * * *